United States Patent [19]

Blatt et al.

[11] E Patent Number: Re. 32,089

[45] Reissued Date of Patent: Mar. 4, 1986

[54] BLOOD FRACTIONATING PROCESS AND APPARATUS FOR CARRYING OUT SAME

[75] Inventors: William F. Blatt, Framingham; Edward A. Agranat, Weston; Peter N. Rigopulos, Melrose, all of Mass.

[73] Assignee: Amicon Corporation, Lexington, Mass.

[21] Appl. No.: 235,093

[22] Filed: Feb. 17, 1981

Related U.S. Patent Documents

Reissue of:

[64] Patent No.: 3,705,100
Issued: Dec. 5, 1972
Appl. No.: 66,675
Filed: Aug. 25, 1970

[51] Int. Cl.[4] ..... B01D 13/00

[52] U.S. Cl. ..... 210/651; 210/433.2; 210/456; 210/927

[58] Field of Search ..... 128/214 R, 224; 210/DIG. 927, 433 M, 651, 456, 321.1, 433.2

[56] References Cited

U.S. PATENT DOCUMENTS

| | | | |
|---|---|---|---|
| 3,448,041 | 6/1969 | Swank | 210/DIG. 23 |
| 3,483,867 | 12/1969 | Markovitz | 210/433 M |
| 3,488,768 | 1/1970 | Rigopulos | 210/23 F |
| 3,539,300 | 11/1970 | Stone | 23/253 |
| 3,560,377 | 2/1971 | Loeffler | 210/456 X |
| 3,567,031 | 3/1971 | Loeffler | 210/456 X |

OTHER PUBLICATIONS

Bixler et al., "The Development of a Diafiltration System for Blood Purification", from Trans. Amer. Soc. Artif. Int. Organs, vol. XIV, Jun. 14, 1968, 99–108.

*Primary Examiner*—Frank Spear

[57] ABSTRACT

A process for separating blood plasma from whole blood that dispenses with the known centrifugal-separation techniques and involves passing whole blood along a flow path which is shallow and substantially parallel to the upstream side of filtration membrane, recovering plasma from the downstream side of said membrane, and recovering the retained blood components (formed elements) from the upstream side of the membrane.

4 Claims, 4 Drawing Figures

BLOOD FRACTIONATING PROCESS AND APPARATUS FOR CARRYING OUT SAME

Matter enclosed in heavy brackets [ ] appears in the original patent but forms no part of this reissue specification; matter printed in italics indicates the additions made by reissue.

*This application is a continuation of Ser. No. 940,969, filed Sept. 11, 1978, now abandoned, and a reissue of Ser. No. 05/066,675, filed Aug. 25, 1970, now U.S. Pat. No. 3,750,100.*

This application is a continuation-in-part of U.S. Ser. No. 828,935, filed May 29, 1969, now abandoned, and of Ser. No. 833,090, filed June 13, 1969, now abandoned.

When obtaining blood from a blood donor, it is very often desirable to be able to return the cellular components to the donor so that more frequent bleedings can be made. When only the plasma component of the blood is desired for emergency use, the formed elements of the blood (which include the red blood cells, white blood cells and platelets) can be discarded or used for other purposes or can profitably be returned to the donor. Such a return is particularly important because (1) it allows the donor to recuperate to a state where he can donate again within two weeks rather than in about 2 months as is the case when the non-plasma component of the blood is not returned to him, and (2) it avoids the temporary weakness suffered by some donors after they donate a pint of blood. The importance of a donor's being able to contribute blood at relatively frequent intervals is obvious in circumstances such as those wherein injuries are incurred during military operations or wherein a donor bears a rare blood-type for which an emergency need exists.

However, blood fractionating of the type described is not used as frequently as desirable because no really convenient means for carrying out the process has been available. In general, this type of blood-fractionating has been done by (1) transferring the blood from a donor into a blood bag by means known to most blood donors, then
(2) transferring the blood bag into a centrifugal separating apparatus, then
(3) "spinning" the blood at a rate which optimizes the separation of plasma from other blood components, but substantially avoids damage to blood cells, then
(4) separation of plasma by bag compression or withdrawal to a receiving vessel, and finally
(5) returning the formed elements back into the patient by the usual transfusion techniques.

Not only does this process involve relatively expensive apparatus, but it also comprises a sufficiently large number of handling steps to significantly increase the chance of contamination and/or cellular damage in the relatively crude environments of the type that may be encountered at accident scenes, in military operations, etc.

Moreover, there are many situations in which it is desirable to separate blood components without returning any of them to the donor in order to use diagnostic tests without interference from either the formed cell or plasma components thereof.

The present invention provides a process and apparatus for simple fractionation of whole blood into a plasma component and a cellular component while subjecting the components to only very slight stress.

The present invention is furthermore readily applicable to blood-donation procedures, making it possible to return the non-plasma component or fraction to the donor virtually simultaneously with the donation.

The process of the present invention comprises conducting the whole blood in a flow path parallel to one face of a porous filter membrane having effective pore diameters from 0.1 to 0.8 micron, the path having a maximum depth of 20 mils measured vertically from the face of the membrane, collecting from the opposite face of the membrane the plasma component, and collecting from the end of said flow path the cellular component while maintaining the pressure differential between opposite faces of the membrane from 1 to 15 p.s.i. For best results the rate of flow of the whole blood across the face of the membrane is maintained from 2 to 50 ft. per minute and the pore diameter is from 0.4 to 0.7 micron. The precise diameter of the pores within the stated ranges of size which gives best results depends upon the precise pressure differential employed, higher pressure differentials within the stated range requiring smaller pore diameters. The pressure differential is critical because it provides the driving force for controlling the velocity of the blood across, and plasma through the membrane, and also affects the degree of hemolysis which occurs during filtration.

It is essential that the blood being filtered travel in a path substantially parallel to and within 20 mils of the membrane surface. Attempts to utilize the same membranes under conditions whereby the whole blood is forced through the membrane by conventional filtration techniques (i.e., putting the blood in a reservoir over filtration membrane and applying a pressure difference across the membrane to push or pull the plasma fraction through the membrane) results in almost immediate "plugging" of the membrane.

The term "filtration membrane" is used in this application to means that class of filters normally supplied in thin sheet form and capable of effecting separation of very small particulate or molecular components from suspensions or solutions. Both anisotropic and depth-filter membranes are included within this description. The former type of membrane is preferred when conveniently availble, but a particularly surprising feature of the invention is that homogeneous depth filters may be utilized in the blood separation process.

The filtration process of the invention is carried out at relatively low pressure differentials, e.g., from 1 to 15 p.s.i, as measured both from one side of the filter membrane to the other and as measured from the inlet of the whole blood passage to the outlet for the blood fraction which fails to pass through the filter membrane. As a matter of convenience, both the receptable for the filtrate (plasma) and for the rejected blood (non-plasma fraction) are preferably maintained at atmospheric pressure. Pressure differentials near the lower end of this range, i.e., from 1.5 to 5 p.s.i. are most advantageous, in part because they can be utilized in equipment which is less rigorously designed to avoid undue stress on the cells contained in the blood being fractionated. Likewise the velocity across the face of the membrane is relatively low, i.e., in the range of from 2 to 50 feet per minute. Under these conditions, the flow is substantially laminar. In the more preferable embodiments of the invention the blood, after passing over the surface of the membrane, is recycled back to the whole blood reservoir. The velocity of the stream being dissipated in the contents of the reservoir aids in keeping the blood mixed well.

In order to point out more fully the nature of the present invention, the following specific example is given as an illustrative embodiment of the present process and products produced thereby.

Figure 1:
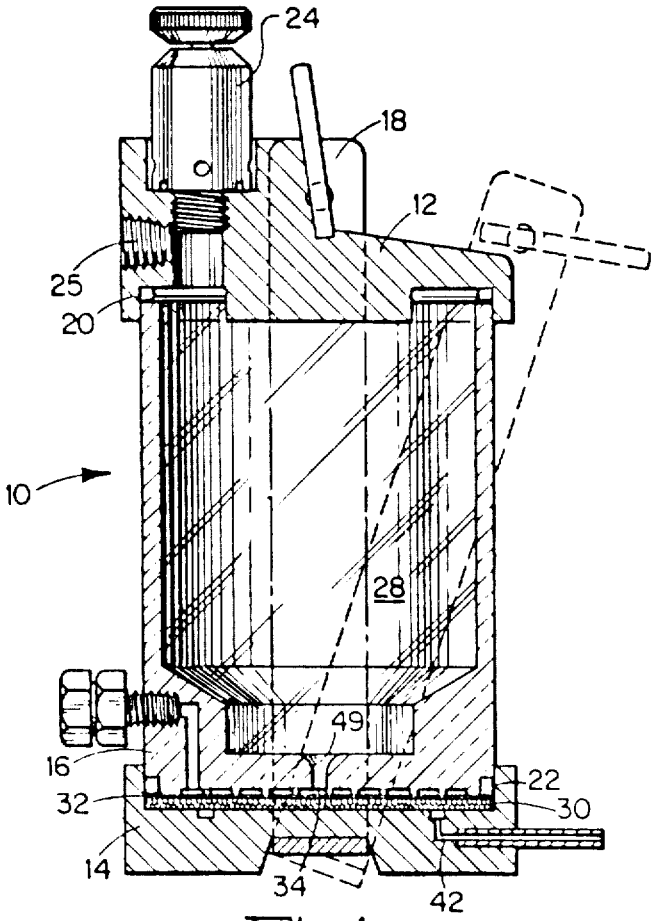
FIG. 1 shows a view in elevation, partly in section, of a thin channel ultrafiltration cell useful for carrying out the process of the invention.
Figure 2:
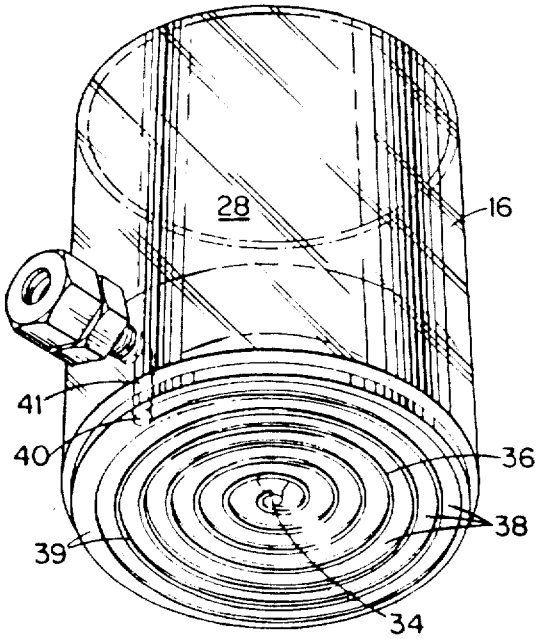
FIG. 2 is a perspective view from the bottom of the reservoir and flow-directing means showing the apparatus of FIG. 1.

Referring to FIGS. 1 and 2, it is seen that an ultrafiltration cell 10 comprises a top cap 12, a bottom cap 14 and a cylinder assembly 16. The cylinder is compressed and sealed between caps 12 and 14 by means of toggle clamping assembly 18, top O-ring seal 20, and bottom O-ring seal 22.

Top cap 12 comprises a pressure relief valve 24 and a means to drive fluid across the membrane comprising a port 25 adapted for connection to a pressurized gas source for pressurizing liquid in reservoir 28.

Resting on bottom cap 14 is a macroporous support plate 30 formed of sintered polypropylene. Over plate 30 is a cellulosic ester filtration membrane 32 having a mean pore size of $0.45 \pm 0.02$ micron and available from Millipore Corporation under the trade designation HAW PO 9025. Lower O-ring seal 22 is compressed against the outer periphery of membrane 32, thereby providing an efficient edge sealing means.

Cylinder assembly 16 comprises reservoir 28 and an aperture 34 leading from reservoir 28 into a spiral flow path 36 which is formed by spiral grooves 38 on the bottom surface 39 of assembly 16. This flow path 36 is 0.125 inch wide and 0.010 inch (10 mils) high. It follows a spiral path in a plane parallel to the membrane surface, terminating at a fluid outlet port 40 through which the retained liquid may, via conduit 41, be collected or recycled for another concentrating step. Filtrate, i.e., that fraction of material which comes through the filter is carried out of the cell through conduit 42 which is machined into bottom cap 14.

A sample of whole blood (treated with ACD) was inserted into reservoir 28 and, under a 2 p.s.i.g. driving force, was divided into a plasma fraction and a cellular fraction. The whole blood was forced through aperture 34 in cylinder assembly 16, and thereupon is caused to follow spiral flow path 36 over the surface of membrane 32. The blood plasma fraction passed through the filtration membrane, and was collected through conduit 41 at atmospheric pressure. About 60% of the plasma content of the blood was recovered and there was no evidence of hemolysis in the plasma so collected.

Although the optimum operation of the illustrated device was realized with an operating pressure of from 2 to 4 p.s.i.g., it is stressed that higher operating pressures may be used when particular care is taken to smooth blood-contacting surfaces in such a way as to avoid excessive mechanical shear on the formed elements of the blood. For example, a stream-lined or smooth-surfaced wall 49 with gently rounded corners of aperture 34 is advantageous in this respect. In general, however, a low-pressure process is most desirable for use in emergency blood-donation procedures.

Figure 3:
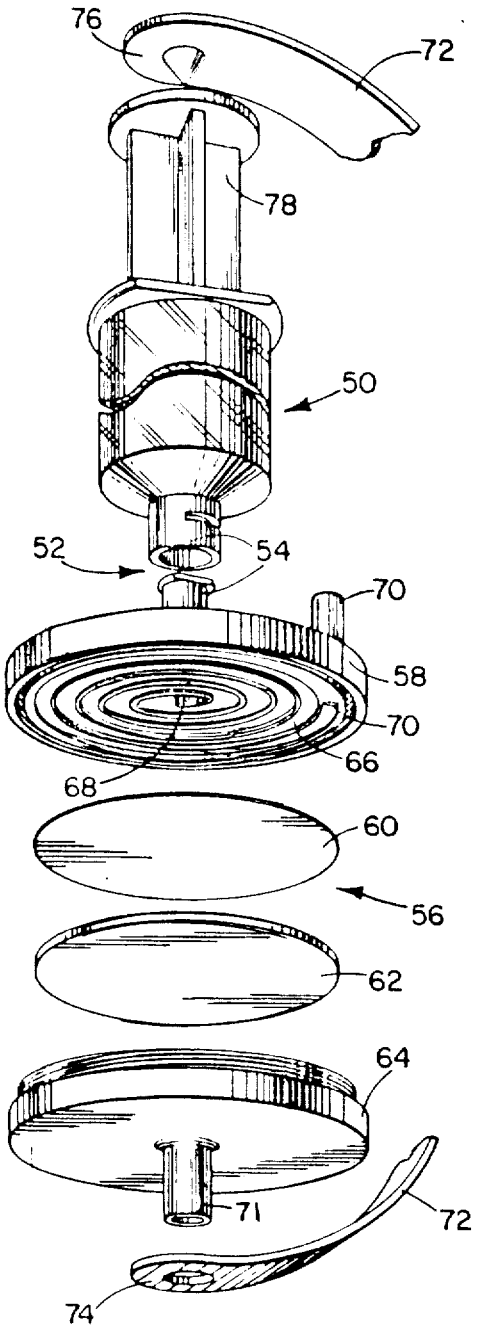
FIG. 3 is an exploded view in perspective showing a novel apparatus useful in the process of another embodiment of the invention which comprises a means to attach a hypodermic needle thereto.

Another embodiment of the apparatus is disclosed in FIG. 3. In this apparatus, which is most useful in analytical work, a hypodermic syringe 50 has been utilized to withdraw a blood sample from a patient. The needle (not shown) of the syringe is then removed and the syringe is attached, by means of a fastening means 52, such as Luer lock 54, to filtration cell 56. Filtration cell 56 comprises a top retaining plate 58, filtration membrane 60, a sintered porous polyethylene support disk 62, and a bottom retaining plate 64.

Retaining plate 58 comprises a spiral ridge forming a shallow flow path 66 having a depth of 6 mils, a width of 0.5 cm. and a length of 70 cm. between inlet port 68 and outlet port 70. Retaining plate 64 comprises a filtration outlet port 71.

In order to achieve the most reproducible filtration results, it has been found more desirable to provide the above-described apparatus with a positive pressure control means rather than to rely upon the manual pressure exerted by a number of different operators. Therefore, a spring means 72 is mounted, at one end 74 thereof, on projecting outlet port 70. The other end 76 of the spring is adapted to press on plunger 78 of the hypodermic syringe 50. When spring means 72 is so mounted as to rest on plunger 78, a controlled amount of pressure, about 2.5 p.s.i., is generated for filtering the blood. Another advantage is that one operator can utilize a number of these devices at a single time since they do not require close attention during the filtration operation.

Figure 4:
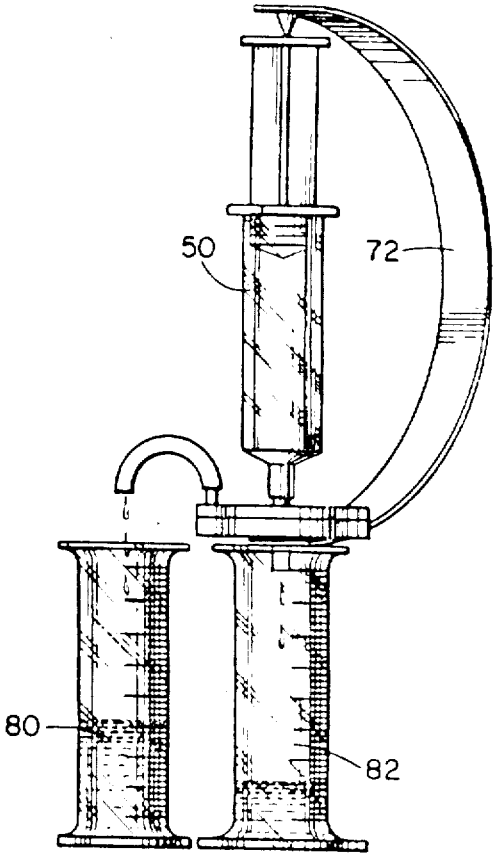
FIG. 4 is a view in elevation showing the apparatus of FIG. 3 in operation.

FIG. 4 shows a schematic diagram showing the analytical device of FIG. 3 in operation. A plasma fraction of the blood is being collected in vessel 82 while the other blood components are being collected in vessel 80.

Using the cellulosic ester membrane described above, less than 0.1% hemolysis was observed, and the plasma obtained was not detectably different from that obtained by conventional centrifugation. From a 10 ml. sample of fresh blood of normal hematocrit, there was obtained, in a filtering time of 15 to 20 minutes, approximately 3.0 to 3.4 ml. of plasma. Similar results were obtained using under the same conditions a polycarbonate membrane 1–10 mils thick) having a pore size of $0.5 \pm 0.06$ microns available under the trademark Nuclepore from the General Electric Company.

Various other advantages and modifications will be apparent to those skilled in the art and fall within the scope of the appended claims.

We claim:

[1. Apparatus constructed and arranged to carry out a separation of whole blood into a plasma fraction and a cellular fraction, said apparatus comprising (1) a reservoir for holding whole blood which is to be fractionated, (2) a filtration membrane having a pore size from about 0.1 to 0.8 micron diameter, (3) a flow directing means adjacent one side of said membrane for conducting whole blood from said reservoir across the face of said membrane in a zone having a maximum depth of 20 mils measured vertically from the face of said membrane, and (4) pressure-generating means constructed and arranged to drive said whole blood to be fractionated through said flow path only within the range of a pressure differential from 1 to 15 p.s.i. and at a flow velocity across the face of the membrane from 2 to 50 feet per minute.]

[2. Apparatus as defined in claim 1 wherein said reservoir is formed of the barrel of a hypodermic syringe, wherein said pressure-generating means comprises the piston of a hypodermic syringe, and wherein said syringe is detachably connected to said membrane and flow directing means.]

[3. Apparatus as defined in claim 1 wherein said filtration membrane has a pore size from about 0.4 to about 0.7 micron in diameter.]

[4. Apparatus as defined in claim 2 comprising additionally a spring for automatically operating the piston of said hypodermic syringe.]

5. A process for separating blood plasma from the other components of blood *without substantial hemolysis* comprising the steps of (1) conducting whole blood in a flow path which is substantially parallel to the upstream side of a filtration membrane and has a maximum depth of 20 mils measured vertically from the face of the membrane, said membrane having a pore size from about 0.1 to about 0.8 micron in diameter, (2) applying sufficient pressure to said whole blood to cause *a* pressure differential from 1 to 15 p.s.i. between upstream and downstream sides of said membrane and to provide a flow velocity across the face of the membrane from 2 to 50 feet per minute, (3) recovering plasma ultrafiltrate from the downstream side of said membrane, and (4) recovering the retained blood components from the upstream side of the membrane,

*said plasma ultrafiltrate being substantially free of evidence of hemolysis.*

6. A process as defined in claim 5 wherein said filtration membrane has a pore size from about 0.4 to about 0.7 micron in diameter.

7. A process as defined in claim 6 wherein the pressure differential is from 2 to 5 p.s.i.

8. In a process for removing whole blood from a blood donor and returning the blood constituents to the donor while keeping the plasma for medical use, the improvement consisting of (1) transferring said whole blood from said donor into contact with the upstream side of filtration membrane having a pore size from about 0.1 to about 0.8 micron in diameter, (2) conducting said whole blood across the surface of the membrane in a path which is substantially parallel to the upstream side of said membrane and has a maximum depth of 20 mils measured vertically from the face of the membrane, (3) applying sufficient pressure to said whole blood to provide a pressure differential of 1 to 15 p.s.i. between upstream and downstream sides of said membrane and to provide a flow velocity across the face of the membrane from 2 to 50 feet per minute, and (4) recovering the retained blood components from the upstream side of the membrane and transferring them back to the blood donor,

*said plasma being removed from the downstream side of said membrane and being substantially free of evidence of hemolysis.*

* * * * *